(12) United States Patent
Lee et al.

(10) Patent No.: US 9,563,946 B2
(45) Date of Patent: Feb. 7, 2017

(54) OVERLAY METROLOGY METHOD AND OVERLAY CONTROL METHOD AND SYSTEM

(71) Applicant: TAIWAN SEMICONDUCTOR MANUFACTURING CO., LTD., Hsinchu (TW)

(72) Inventors: Yung-Yao Lee, Zhubei (TW); Ying-Ying Wang, Xin-Zhu (TW); Shang-Wern Chang, Zhubei (TW); Heng-Hsin Liu, New Taipei (TW)

(73) Assignee: TAIWAN SEMICONDUCTOR MANUFACTURING CO., LTD., Hsinchu (TW)

( * ) Notice: Subject to any disclaimer, the term of this patent is extended or adjusted under 35 U.S.C. 154(b) by 26 days.

(21) Appl. No.: 14/338,041

(22) Filed: Jul. 22, 2014

(65) Prior Publication Data

US 2016/0025650 A1    Jan. 28, 2016

(51) Int. Cl.
*G01B 11/00*  (2006.01)
*G06T 7/00*  (2006.01)
*G01N 21/956*  (2006.01)
*G01N 21/88*  (2006.01)

(52) U.S. Cl.
CPC ............ *G06T 7/001* (2013.01); *G01N 21/956* (2013.01); *G01N 21/95607* (2013.01); *G01N 21/8851* (2013.01); *G01N 2021/8887* (2013.01); *G06T 2207/30148* (2013.01)

(58) Field of Classification Search
CPC ............ G03F 7/00; G03F 9/00; Y10S 414/00; Y10S 438/00; H01L 21/00; H01L 23/00; H01L 22/00; G01N 21/00

USPC .................................................. 356/399–401
See application file for complete search history.

(56) References Cited

U.S. PATENT DOCUMENTS

| | | | | |
|---|---|---|---|---|
| 5,784,167 A * | 7/1998 | Ho | ........ | G01B 11/065 356/369 |
| 5,883,720 A * | 3/1999 | Akiyama | ........... | G01B 11/0625 356/632 |
| 6,884,552 B2 * | 4/2005 | Mieher | ................ | G06K 7/0095 356/401 |
| 7,218,399 B2 * | 5/2007 | Hayano | ............... | G03F 7/70633 356/401 |
| 8,860,941 B2 * | 10/2014 | Lee | ........ | G01B 11/00 356/401 |
| 2002/0098426 A1 * | 7/2002 | Sreenivasan | ........ | B29C 35/0888 430/22 |
| 2002/0180961 A1 * | 12/2002 | Wack | ........ | G01N 21/211 356/237.2 |

\* cited by examiner

*Primary Examiner* — Tarifur Chowdhury
*Assistant Examiner* — Isiaka Akanbi
(74) *Attorney, Agent, or Firm* — Maschoff Brennan (57) ABSTRACT

The present disclosure provides an overlay metrology method, an overlay control method and an overlay control system. The overlay metrology method includes capturing a current layer image of a current overlay mark on a current layer with a current focal length and capturing a previous layer image of a previous overlay mark on a previous layer with a previous focal length. Then, the overlay metrology method further includes combining the current layer image with the previous layer image to form an overlay mark image and determining an overlay error between the current overlay mark and the previous overlay mark based on the overlay mark image.

20 Claims, 9 Drawing Sheets

OVERLAY METROLOGY METHOD AND OVERLAY CONTROL METHOD AND SYSTEM

BACKGROUND

The present disclosure relates to overlay metrology.

As technology advances, the integrated circuit (IC) industry has experienced exponential growth. Technological advances in layering, patterning and doping operations have produced generations of ICs where each generation has smaller and more complex circuits than the previous generation. In the course of IC evolution, functional density, such as the number of interconnected devices, has generally increased while geometry size has decreased. Meanwhile, a wafer size has increased for manufacturing more ICs on one single wafer. Thus during fabrication of semiconductor devices, each patterned layer has to be aligned with a previous patterned layer.

Currently, the alignment precision is measured as overlay offset or overlay error. The overlay is the relative position between two or more layers of a wafer. As semiconductor processes evolve to provide for smaller critical dimensions, and devices reduce in size and increase in complexity including number of layers, the alignment precision between layers becomes increasingly more important to the quality, reliability, and yield of the devices. Misalignment of layers can cause performance issues and even potentially causing a device to fail due to, for example, a short caused by a misaligned interconnect layer.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification, specify the presence of stated features, regions, integers, operations, operations, elements, and/or components, but do not preclude the presence or addition of one or more other features, regions, integers, operations, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 1:
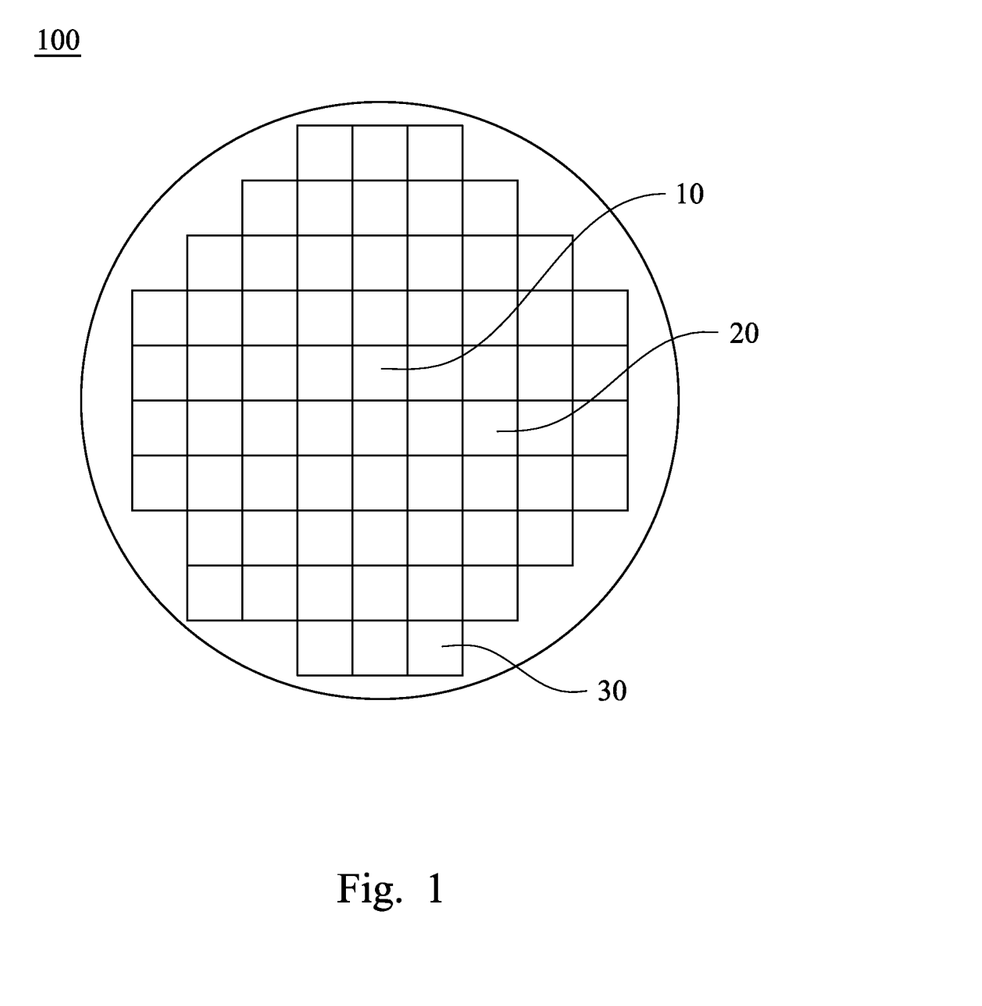
FIG. 1 is a top view of a wafer in accordance with some embodiments of the present disclosure.
Figures 2, 3:
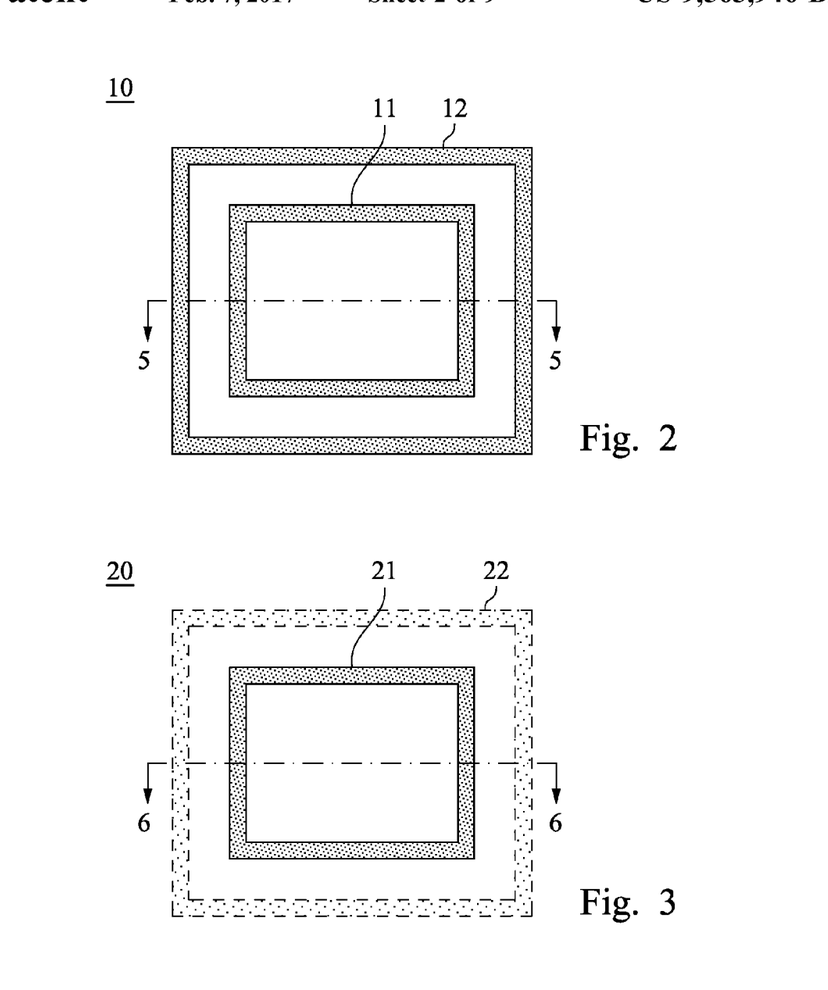
FIGS. 2, 3 and 4 show overlay mark image in three different fields of FIG. 1.
Figure 4:
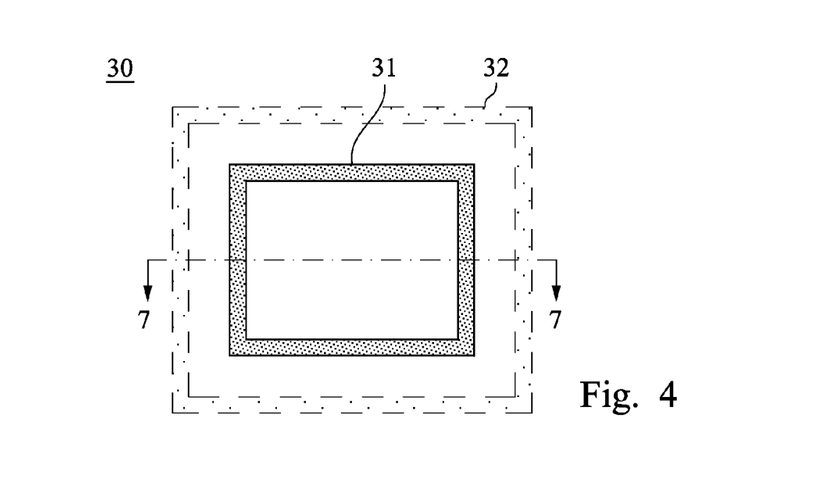

As aforementioned, misalignment of layers may cause performance issues and even potentially causing a device to fail, and therefore the overlay error between layers during fabrication should be measured adequately to allow for possible correction. In some embodiments of the present disclosure, an overlay metrology method using optically readable overlay marks formed on layers of a wafer during fabrication is provided. FIG. 1 is a top view of a wafer 100 in accordance with some embodiments of the present disclosure. FIGS. 2-4 show overlay mark images in three different fields 10, 20, and 30 of FIG. 1.

As shown in FIG. 2, the overlay marks include an inner box 11 and an outer box 12. The inner box 11 is disposed within the outer box 12. The inner box 11 is formed on a current layer of the wafer 100 while the outer box 12 is formed on a previous layer under the current layer of the wafer 100. However, the present disclosure should not be limited to such arrangement. In some embodiments, the inner box is formed on the previous layer while the outer box is formed on the current layer. An overlay error is determined by measuring a distance between the center of the inner box 11 and the center of the outer box 12. It should be understood that in other types of overlay marks, for example box-in-bar overlay marks or bar-in-bar overlay marks, the overlay error can also be determined by measuring a displacement of the center point between the bar and the bar/box. It should be understood that although overlay marks shown in FIGS. 2-4 are box-in-box targets, the overlay marks are not limited to the box-in-box targets. Other overlay marks which allow the overlay error to be determined by measuring a distance between the centers of the overlay marks can be used as well. For example, in some embodiments, the overlay marks can be bar-in-box targets or bar-in-bar targets.

Figure 5:
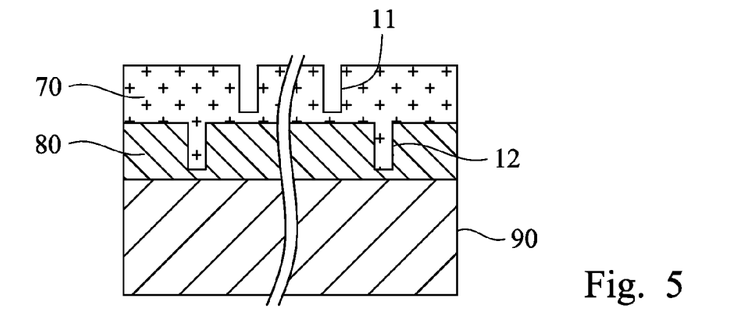
FIG. 5 is a sectional view taken along the line 5 of FIG. 2.
Figure 6:
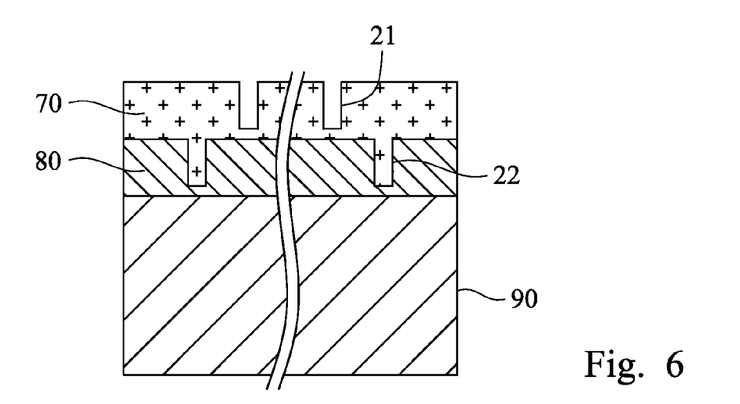
FIG. 6 is a sectional view taken along the line 6 of FIG. 3.
Figure 7:
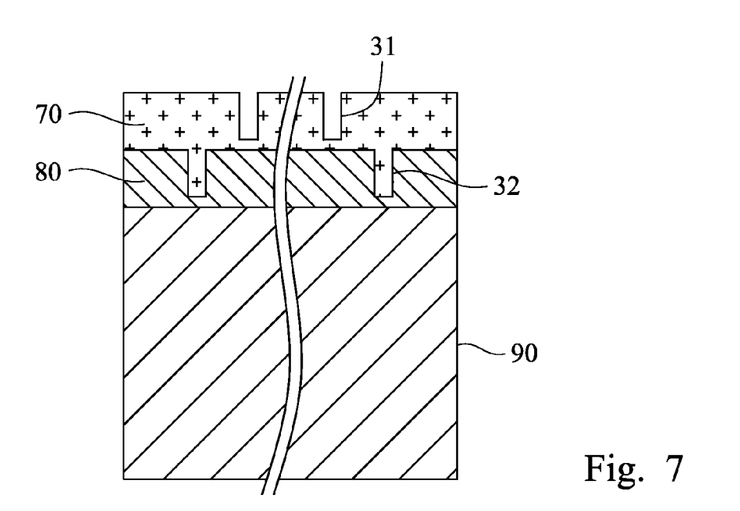
FIG. 7 is a sectional view taken along the line 7 of FIG. 4.

As the size of the wafer 100 increases, the previous layer or the layer adjacent to the previous layer may have different thicknesses in the fields 10, 20 and 30 due to the process variation. FIG. 5 is a sectional view taken along the line 5 of FIG. 2. FIG. 6 is a sectional view taken along the line 6 of FIG. 3. FIG. 7 is a sectional view taken along the line 7 of FIG. 4. As shown in FIGS. 5-7, the previous layer 80 is disposed under the current layer 70. A dielectric layer 90 is disposed under the previous layer 80. The dielectric layer 90 has a thickness variation among the fields 10, 20 and 30. The thickness variation of the dielectric layer 90 increases as the size of the wafer 100 increases. For example, the dielectric layer in an 18 inch wafer has a thickness variation about 2.25 times greater than that in a 12 inch wafer.

Since the dielectric layer 90 is transparent to light, the dielectric layer 90 affects autofocus performance when capturing the overlay mark images of FIGS. 2-4. When the dielectric layer 90 is thinner than a predetermined thickness, the dielectric layer 90 insignificantly affects the autofocus performance. Therefore, as shown in FIG. 2, the inner box 11 is in focus, and the outer box 12 is in focus as well. However, when the dielectric layer 90 is thicker than the predetermined thickness, the dielectric layer 90 significantly affects the autofocus performance. As shown in FIGS. 3 and 4, although the inner boxes 21 and 31 are in focus, the outer boxes 22 and 32 are out of focus. Therefore, the outer boxes 22 and 32 are blur or less visible, causing the overlay errors to be inaccurately determined.

Figure 8:
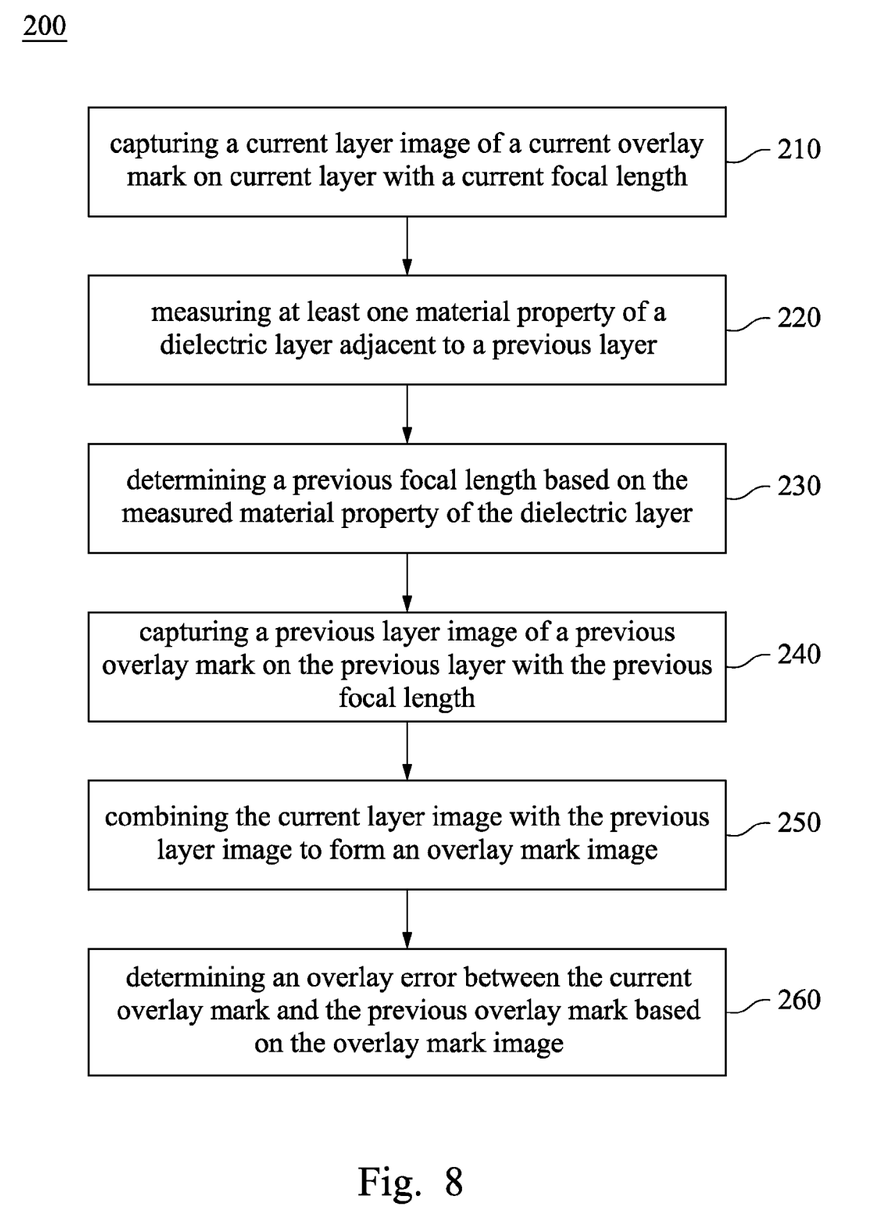
FIG. 8 is a flow chart of an overlay metrology method in accordance with some embodiments of the present disclosure.

FIG. 8 is a flow chart of an overlay metrology method 200 in accordance with some embodiments of the present disclosure. The overlay metrology method 200 includes the following operations. A current layer image of a current overlay mark on a current layer is captured with a current focal length (operation 210). At least one material property of a dielectric layer adjacent to a previous layer is measured (operation 220). A previous focal length is determined based on the measured material property of the dielectric layer (operation 230). A previous layer image of a previous overlay mark on the previous layer is captured with the previous focal length (operation 240). The current layer image is combined with the previous layer image to form an overlay mark image (operation 250). An overlay error between the current overlay mark and the previous overlay mark is determined based on the overlay mark image (operation 260). The following description illustrates how to perform the aforementioned operations 210-260 with reference to FIGS. 7-8.

In operation 210, the current layer image of the inner box 31, i.e. the current overlay mark, on the current layer 70 is captured with the current focal length. The current layer image is an image where the inner box 31 is in focus. The current focal length for capturing the current layer image can be determined by, for example, an autofocus system. The autofocus point or points of the autofocus system are on the inner box 31 to ensure the inner box 31 in the current layer image is in focus. The autofocus system can be active or passive. The active autofocus system measures a distance to the inner box 31 and subsequently determines the current focal length based on the measured distance. The passive autofocus system determines the current focal length by performing passive analysis of the image that is entering the autofocus system. Passive autofocusing can be achieved by, for example, phase detection autofocus or contrast detection autofocus.

In operation 220, at least one material property of the dielectric layer 90 under the previous layer 80 is measured by, for example, an ellipsometer, but is not limited thereto. The ellipsometer can be used to characterize composition, roughness, thickness (depth), crystalline nature, doping concentration, electrical conductivity, and other material properties. In order to measure the material properties, e.g. the thickness, of the dielectric layer 90, a light source of the ellipsometer applies polarized light to the surface of the dielectric layer 90. After reflection, the reflected light falls into a detector of the ellipsometer. Then, an analyzer of the ellipsometer determines the material properties, e.g. the thickness, of the dielectric layer 90 by measuring the change of polarization upon the reflection and comparing it to a model.

In operation 230, the previous focal length is determined based on at least the measured thickness of the dielectric layer 90. In some embodiments, the previous focal length is determined by the following equation:

$$F_P = F_c + \alpha T,$$

where $F_P$ is the previous focal length, $F_c$ is the current focal length, $\alpha$ is a coefficient related to the material of the dielectric layer 90, T is the measured thickness of the dielectric layer 90.

More specifically, $\alpha$ in the equation is a coefficient related to the dielectric constant and/or the refractive index of the dielectric layer 90. The dielectric constant and/or the refractive index of the dielectric layer 90 can be measured by the ellipsometer as well. Since the dielectric constant and/or the refractive index of the dielectric layer 90 may affect the autofocus performance, the previous focal length is determined further based on the dielectric constant and/or the refractive index of the dielectric layer 90. In short, the previous focal length is determined based on at least one of the thickness, the dielectric constant and the refractive index of the dielectric layer 90.

In operation 240, the previous layer image of the outer box 32 on the previous layer 80 is captured with the previous focal length.

Figure 9:
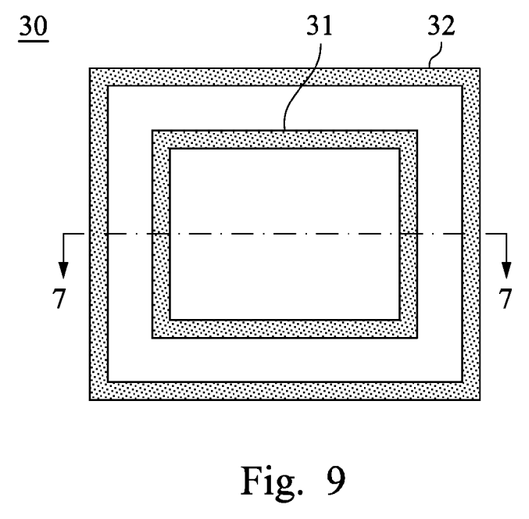
FIG. 9 shows the overlay mark image formed by superimposing a current layer image on a previous layer image in accordance with some embodiments of the present disclosure.

In operation 250, the current layer image is combined with the previous layer image to form the overlay mark image. In some embodiments, the overlay mark image is formed by superimposing the current layer image on the previous layer image. FIG. 9 shows the overlay mark image formed by superimposing the current layer image on the previous layer image in accordance with some embodiments of the present disclosure. As shown in FIG. 9, since the current layer image and the previous layer image are individually captured with appropriate focal lengths, both the inner box 31 and the outer box 32 are in focus.

In operation 260, the overlay error between the inner box 31 and the outer box 32 is determined based on the overlay mark image of FIG. 9. In some embodiments, the overlay error is determined by measuring a distance between the center of the inner box 31 and the center of the outer box 32 in the overlay mark image and then scaling the measured distance to the actual distance, i.e. the overlay error.

Figure 10:
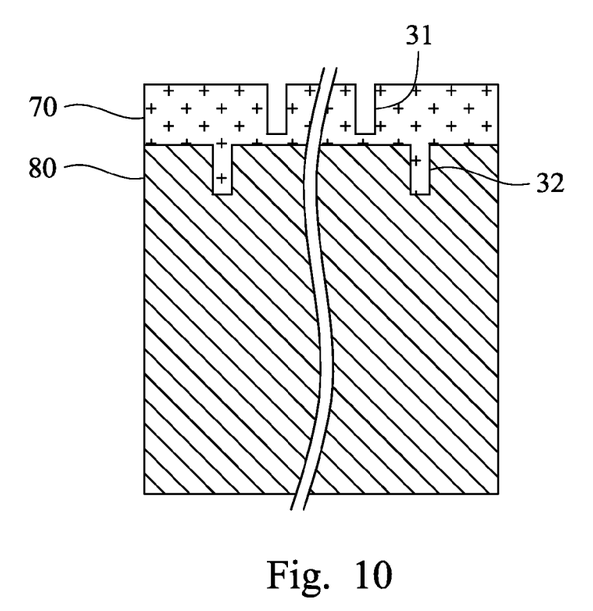
FIG. 10 is a sectional view of a field in accordance with some embodiments of the present disclosure.

FIG. 10 is a sectional view of the field 30 in accordance with some embodiments of the present disclosure. As shown in FIG. 10, in some embodiments, the previous layer 80 may have a thickness variation among different fields. Similarly, when the previous layer 80 is thicker than a predetermined thickness, the previous layer 80 also affects the autofocus performance, causing the overlay error to be inaccurately determined.

Figure 11:
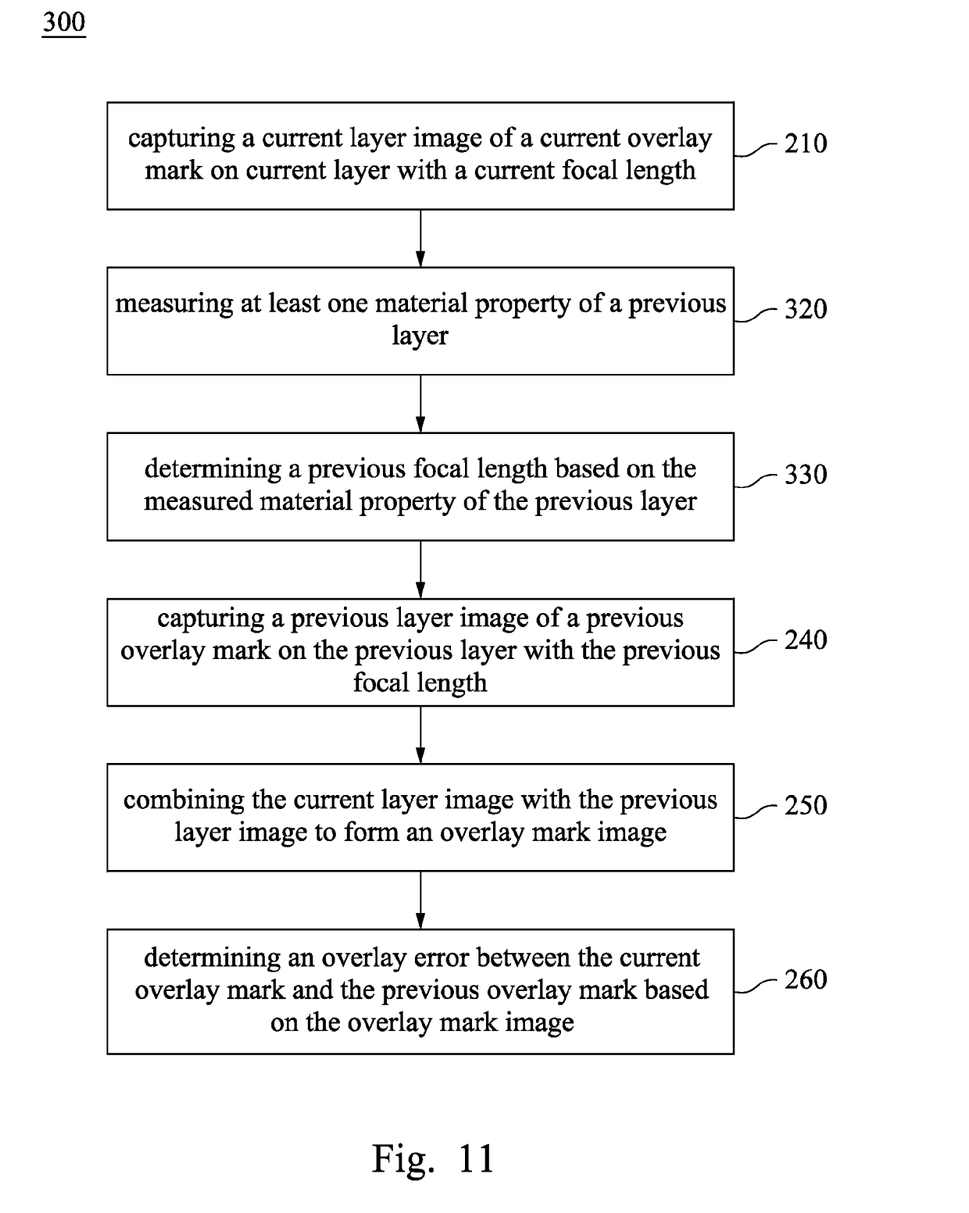
FIG. 11 is a flow chart of an overlay metrology method in accordance with some embodiments of the present disclosure.

FIG. 11 is a flow chart of an overlay metrology method 300 in accordance with some embodiments of the present disclosure. Reference is made to FIGS. 10-11. The overlay metrology method 300 includes the following operations. A current layer image of the inner box 31, i.e. the current overlay mark, on the current layer 70 is captured with a current focal length (operation 210). At least one material property, e.g. the thickness, the dielectric constant, and/or the refractive index, of the previous layer 80 is measured (operation 320). A previous focal length is determined based on the measured material property of the previous layer 80 (operation 330). A previous layer image of the outer box 32, i.e. the previous overlay mark, on the previous layer 80 is captured with the previous focal length (operation 240). The current layer image is combined with the previous layer image to form an overlay mark image (operation 250). An overlay error between the current overlay mark and the previous overlay mark is determined based on the overlay mark image (operation 260).

Similarly, since the current layer image and the previous layer image are individually captured with appropriate focal lengths, both the inner box 31 and the outer box 32 in the overlay mark image are in focus. Therefore, the overlay error between the inner box 31 and the outer box 32 can be properly determined based on the overlay mark image.

Other details regarding the overlay metrology method 300 of FIG. 11 are similar to the overlay metrology method 200 of FIG. 8 and therefore are not repeated here to avoid duplicity.

Figure 12:
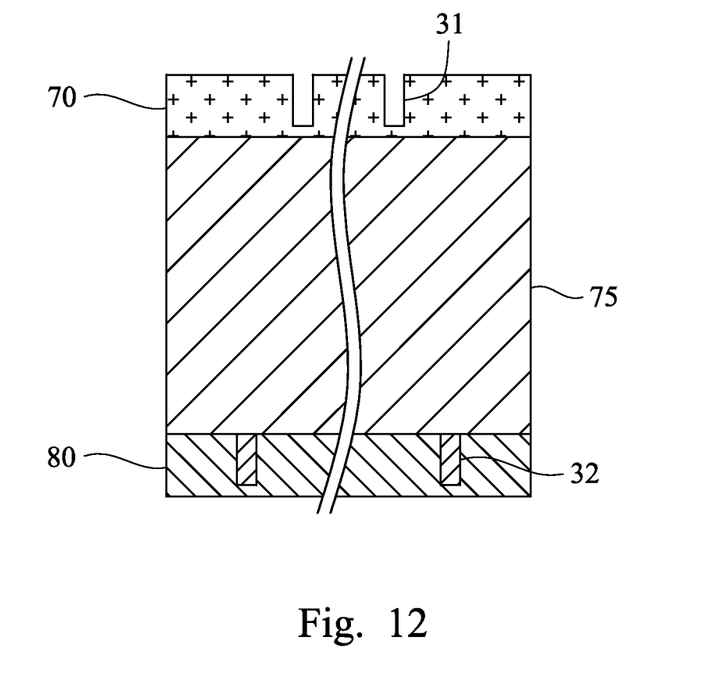
FIG. 12 is a sectional view of a field in accordance with some embodiments of the present disclosure.

FIG. 12 is a sectional view of the field 30 in accordance with some embodiments of the present disclosure. As shown in FIG. 12, in some embodiments, a dielectric layer 75 is disposed between the current layer 70 and the previous layer 80. The dielectric layer 75 has a thickness variation among different fields. Similarly, when the dielectric layer 75 is thicker than a predetermined thickness, the dielectric layer 75 also affects the autofocus performance, causing the overlay error to be inaccurately determined.

Figure 13:
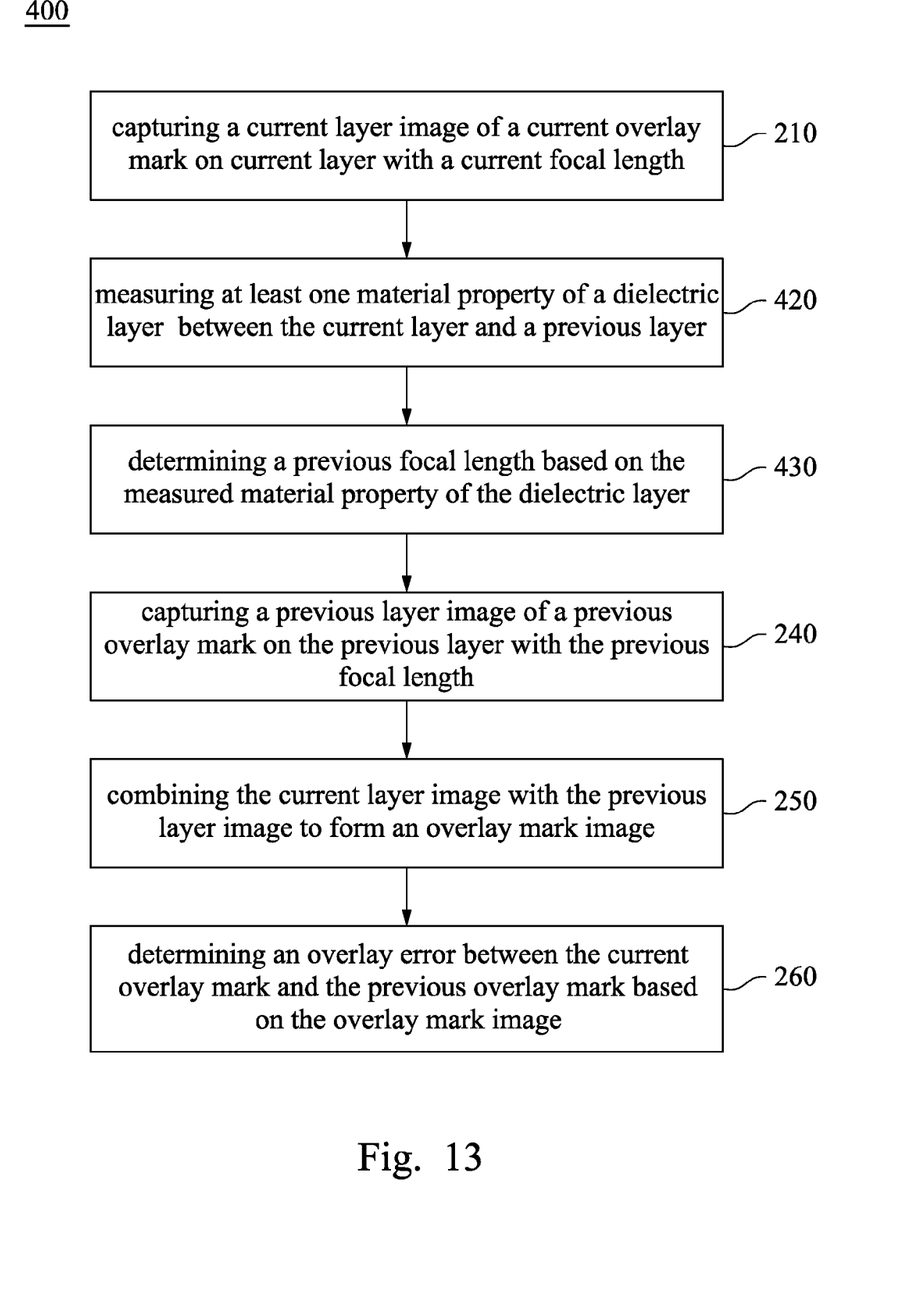
FIG. 13 is a flow chart of an overlay metrology method in accordance with some embodiments of the present disclosure.

FIG. 13 is a flow chart of an overlay metrology method 400 in accordance with some embodiments of the present disclosure. Reference is made to FIGS. 12-13. The overlay metrology method 400 includes the following operations. A current layer image of the inner box 31, i.e. the current overlay mark, on the current layer 70 is captured with a current focal length (operation 210). At least one material property, e.g. the thickness, the dielectric constant, and/or the refractive index, of the dielectric layer 75 is measured (operation 420). A previous focal length is determined based on the measured material property of the dielectric layer 75 (operation 430). A previous layer image of the outer box 32, i.e. the previous overlay mark, on the previous layer 80 is captured with the previous focal length (operation 240). The current layer image is combined with the previous layer image to form an overlay mark image (operation 250). An overlay error between the current overlay mark and the previous overlay mark is determined based on the overlay mark image (operation 260).

Similarly, since the current layer image and the previous layer image are individually captured with appropriate focal lengths, both the inner box 31 and the outer box 32 in the overlay mark image are in focus. Therefore, the overlay error between the inner box 31 and the outer box 32 can be properly determined based on the overlay mark image.

Other details regarding the overlay metrology method 400 of FIG. 13 are similar to the overlay metrology method 200 of FIG. 8 and therefore are not repeated here to avoid duplicity.

Figure 14:
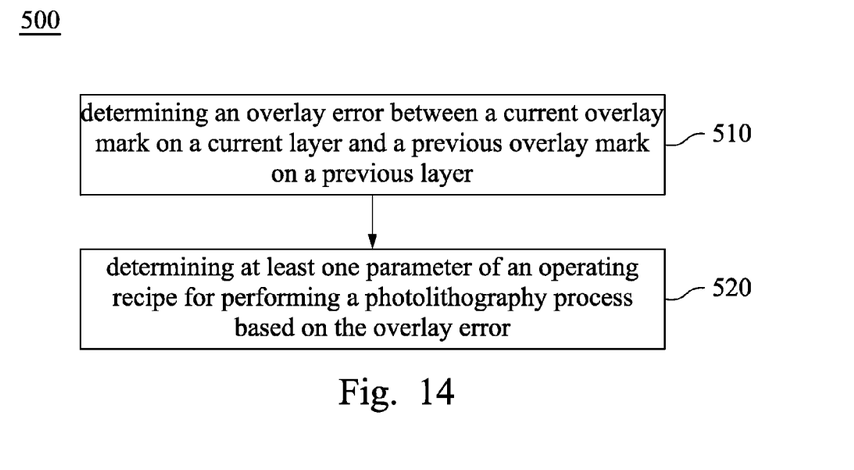
FIG. 14 is a flow chart of an overlay control method in some embodiments of the present disclosure.

FIG. 14 is a flow chart of an overlay control method 500 in accordance with some embodiments of the present disclosure. The overlay control method 500 includes the following operations. An overlay error between a current overlay mark on a current layer and a previous overlay mark on a previous layer is determined according to the aforementioned overlay metrology method 200, 300, or 400 (operation 510). At least one parameter of an operating recipe for performing a photolithography process is determined based on the overlay error (operation 520).

The overlay control method 500 provides feedback to a photolithography tool. After the current layer is patterned by the photolithography tool, the overlay error between the current layer and the previous layer is measured. The feedback generated from the overlay error measurement is provided to the photolithograph tool to update the operating recipe for subsequently processed wafers.

In some embodiments, the at least one parameter of the operating recipe includes but is not limited to at least one of an x-translation parameter, a y-translation parameter, an x-expansion wafer scale parameter, a y-expansion wafer scale parameter, a reticle magnification parameter, a reticle rotation parameter, a wafer rotation parameter, and a wafer non-orthogonality parameter.

Figure 15:
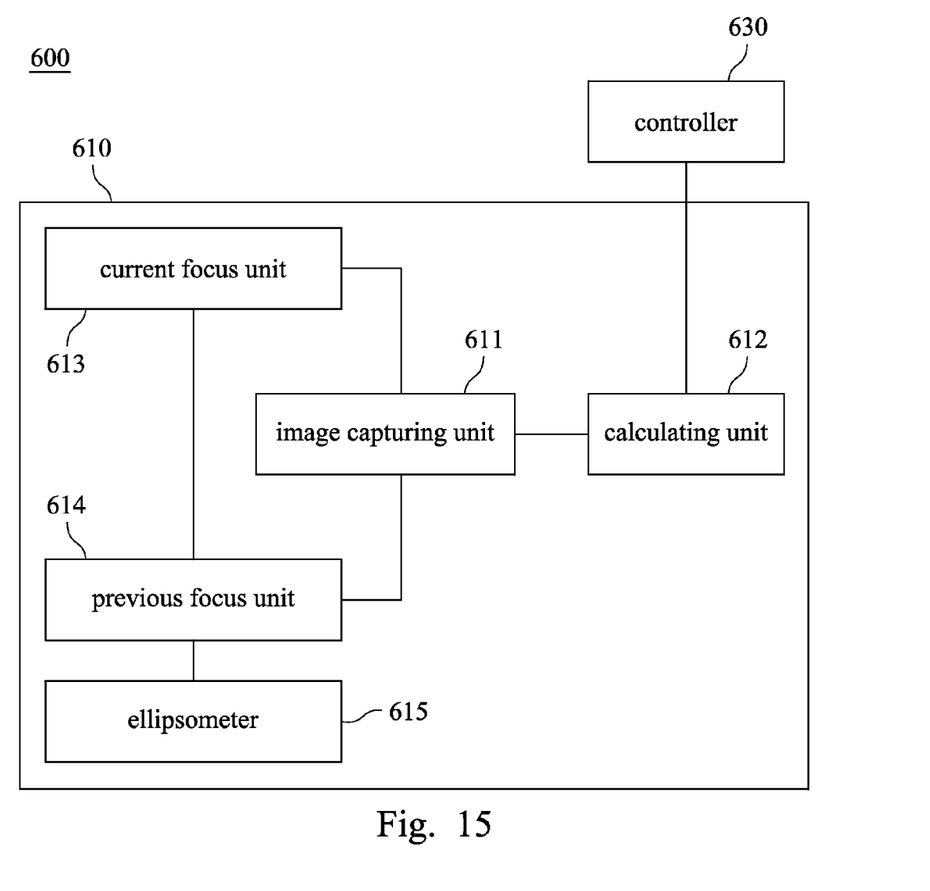
FIG. 15 is a block diagram of an overlay control system in accordance with some embodiments of the present disclosure.

FIG. 15 is a block diagram of an overlay control system 600 in accordance with some embodiments of the present disclosure. As shown in FIG. 15, the overlay control system 600 includes a metrology tool 610 and a controller 630. The metrology tool 610 is configured to determine an overlay error between a current overlay mark on a current layer and a previous overlay mark on a previous layer. The controller 630 is configured to determine at least one parameter of an operating recipe for performing a photolithography process based on the overlay error.

In some embodiments, the metrology tool 610 includes a current focus unit 613, a previous focus unit 614, an ellipsometer 615, a calculating unit 612, and at least one image capturing unit 611. The current focus unit 613 is configured to determine a current focal length. The image capturing unit 611 is configured to capture a current layer image of the current overlay mark on the current layer with the current focal length. The ellipsometer 615 is configured to measure at least one material property of the previous layer and/or a dielectric layer adjacent to the previous layer. The previous focus unit 614 is configured to determine a previous focal length based on the measured material property of the previous layer and/or the dielectric layer adjacent to the previous layer. The image capturing unit 611 is further configured to capture a previous layer image of the previous overlay mark on the previous layer with the previous focal length. The calculating unit 612 is configured to determine the overlay error based on the current layer image and the previous layer image.

In some embodiments, the current focus unit 613 is an autofocus system, such as an active autofocus system or a passive autofocus system. The active autofocus system is, for example, an ultrasonic autofocus system or an infrared autofocus system. The passive autofocus system is, for example, a phase detection autofocus system or a contrast detection autofocus system.

The image capturing unit 611 is, for example, a charge-coupled device (CCD) image sensor or an active-pixel sensor (APS). The APS can be produced by, for example, a complementary metal-oxide-semiconductor (CMOS) or N-type metal-oxide-semiconductor (NMOS) process. The APS produced by the CMOS process is also called a CMOS sensor.

The ellipsometer 615 is an optical system for investigating the dielectric properties (refractive index or dielectric constant) of thin films. The ellipsometer 615 can be used to characterize composition, roughness, thickness (depth), crystalline nature, doping concentration, electrical conductivity, and other material properties. In order to measure the material properties, e.g. the thickness, the dielectric constant, and/or the refractive index, of a thin film, a light source of the ellipsometer applies polarized light to the surface of the thin film. After reflection, the reflected light falls into a detector of the ellipsometer. Then, an analyzer of the ellipsometer determines the material properties, e.g. the thickness, the dielectric constant, and/or the refractive index, of the thin film by measuring the change of polarization upon the reflection and comparing it to a model.

The previous focus unit 614 determines the previous focal length based on at least one of the thickness, the dielectric constant and the refractive index of the previous layer and/or the dielectric layer adjacent to the previous layer. In some embodiments, the previous focal length is determined by the following equation:

$$F_P = F_c + \alpha T,$$

where $F_P$ is the previous focal length, $F_c$ is the current focal length, $\alpha$ is a coefficient related to the material, specifically the dielectric constant and/or the refractive index, of the previous layer and/or the dielectric layer adjacent to the previous layer, T is the thickness of the previous layer and/or the dielectric layer adjacent to the previous layer.

The previous focus unit 614 is, for example, a computer programmed with software to implement the functions described. Alternatively, a hardware calculating unit designed to implement the functions described may also be used.

After the current layer image and the previous layer image are captured, the calculating unit 612 determines the overlay error based on the current layer image and the previous layer image. In some embodiments, the calculating unit 612 may superimpose the current layer image on the previous layer image to form an overlay mark image. Then, the calculating unit 612 may measure a distance between the center of the current overlay mark and the center of the previous overlay mark in the overlay mark image and scale the measured distance to the actual distance, i.e. the overlay error. In some embodiments, the calculating unit 612 is, for example, a computer programmed with software to implement the functions described. Alternatively, a hardware calculating unit designed to implement the functions described may also be used.

The controller 630 provides feedback to a photolithography tool. After the current layer is patterned by the photolithography tool, the metrology tool 610 measures the overlay error between the current layer and the previous layer. The feedback generated from the overlay error measurement is provided to the photolithograph tool to update the operating recipe for subsequently processed wafers.

In some embodiments, the at least one parameter of the operating recipe determined by the controller 630 includes but is not limited to at least one of an x-translation parameter, a y-translation parameter, an x-expansion wafer scale parameter, a y-expansion wafer scale parameter, a reticle magnification parameter, a reticle rotation parameter, a wafer rotation parameter, and a wafer non-orthogonality parameter.

In some embodiments, the controller 630 is, for example, a computer programmed with software to implement the functions described. Alternatively, a hardware controller designed to implement the functions described may also be used.

In order to prevent overlay marks from being out of focus during overlay metrology, an overlay metrology method is designed to individually capture images of a current overlay mark and a previous overlay mark. An overlay error between the current overlay mark and the previous overlay mark is determined based on the individually captured images. Since the images of the current overlay mark and the previous overlay mark are individually captured, both the current overlay mark and the previous overlay mark in the images are in focus. Accordingly, the overlay error can be properly determined.

According to various embodiments of the present disclosure, an overlay metrology method is provided. The overlay metrology method includes capturing a current layer image of a current overlay mark on a current layer with a current focal length, capturing a previous layer image of a previous overlay mark on a previous layer with a previous focal length, combining the current layer image with the previous layer image to form an overlay mark image and determining an overlay error between the current overlay mark and the previous overlay mark based on the overlay mark image.

According to various embodiments of the present disclosure, an overlay control method is provided. The overlay control method includes capturing a current layer image of a current overlay mark on a current layer with a current focal length, capturing a previous layer image of a previous overlay mark on a previous layer with a previous focal length, determining an overlay error between the current overlay mark and the previous overlay mark based on the current layer image and the previous layer image and determining at least one parameter of an operating recipe for performing a photolithography process on the current layer based on the overlay error.

According to various embodiments of the present disclosure, an overlay control system is provided. The overlay control system includes a metrology tool and a controller. The metrology tool includes a current focus unit, a previous focus unit, at least one image capturing unit and a calculating unit. The current focus unit is configured to determine a current focal length. The previous focus unit is configured to determine a previous focal length. At least one image capturing unit is configured to capture a current layer image of a current overlay mark on a current layer with the current focal length and capture a previous layer image of a previous overlay mark on a previous layer with the previous focal length. The calculating unit is configured to determine an overlay error between the current overlay mark and the previous overlay mark based on the current layer image and the previous layer image. The controller is configured to determine at least one parameter of an operating recipe for performing a photolithography process based on the overlay error.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. An overlay control system, comprising:
    a metrology tool comprising:
    a current focus unit configured to determine a current focal length;
    a previous focus unit configured to determine a previous focal length by using at least two independent variables, wherein one of the independent variables is a thickness of a previous layer, a dielectric layer adjacent to the previous layer, or both of them, and another of the independent variables is a coefficient related to a material of the previous layer, the dielectric layer, or both of them;
    at least one image capturing unit configured to capture a current layer image of a current overlay mark on a current layer with the current focal length and capture a previous layer image of a previous overlay mark on the previous layer with the previous focal length; and
    a calculating unit configured to determine an overlay error between the current overlay mark and the previous overlay mark based on the current layer image and the previous layer image; and
    a controller configured to determine at least one parameter of an operating recipe for performing a photolithography process based on the overlay error.

2. The overlay control system of claim 1, wherein the metrology tool further comprises:
    an ellipsometer configured to measure the thickness of the previous layer, and the previous focus unit determines the previous focal length based on at least the measured thickness of the previous layer.

3. The overlay control system of claim 1, wherein the metrology tool further comprises:
    an ellipsometer configured to measure the thickness of the dielectric layer, and the previous focus unit determines the previous focal length based on at least the measured thickness of the dielectric layer.

4. The overlay control system of claim 1, wherein the metrology tool further comprises:
    an ellipsometer configured to measure the coefficient related to the material of the previous layer, and the previous focus unit determines the previous focal length based on at least the measured coefficient related to the material of the previous layer.

5. The overlay control system of claim 1, wherein the metrology tool further comprises:
    an ellipsometer configured to measure the thickness of the previous layer and the coefficient related to the material of the previous layer, and the previous focus unit determines the previous focal length based on at least the measured thickness of the previous layer and the measured coefficient related to the material of the previous layer.

6. The overlay control system of claim 1, wherein the metrology tool further comprises:
    an ellipsometer configured to measure the coefficient related to the material of the dielectric layer, and the previous focus unit determines the previous focal length based on at least the measured coefficient related to the material of the dielectric layer.

7. The overlay control system of claim 1, wherein the metrology tool further comprises:
    an ellipsometer configured to measure the thickness of the dielectric layer and the coefficient related to the material of the dielectric layer, and the previous focus unit determines the previous focal length based on at least the measured thickness of the dielectric layer and the measured coefficient related to the material of the dielectric layer.

8. The overlay control system of claim 1, wherein the metrology tool further comprises:
    an ellipsometer configured to measure a dielectric constant of the previous layer, and the previous focus unit determines the previous focal length based on at least the measured dielectric constant of the previous layer.

9. The overlay control system of claim 1, wherein the metrology tool further comprises:
    an ellipsometer configured to measure a refractive index of the previous layer, and the previous focus unit determines the previous focal length based on at least the measured refractive index of the previous layer.

10. The overlay control system of claim 1, wherein the metrology tool further comprises:
    an ellipsometer configured to measure a dielectric constant of the dielectric layer, and the previous focus unit determines the previous focal length based on at least the measured dielectric constant of the dielectric layer.

11. The overlay control system of claim 1, wherein the metrology tool further comprises:
    an ellipsometer configured to measure a refractive index of the dielectric layer, and the previous focus unit determines the previous focal length based on at least the measured refractive index of the dielectric layer.

12. The overlay control system of claim 1, wherein the current focus unit is configured to determine the current focal length by contrast detection autofocus.

13. The overlay control system of claim 1, wherein the current focus unit is configured to determine the current focal length by phase detection autofocus.

14. An overlay control system, comprising:
    a metrology tool comprising:
    a current focus unit configured to determine a current focal length;
    a previous focus unit configured to determine a previous focal length at least based on a product of a plurality of factors, wherein one of the factors is a thickness of a previous layer, a dielectric layer adjacent to the previous layer, or both of them, and another of the factors is a coefficient related to a material of the previous layer, the dielectric layer, or both of them;
    at least one image capturing unit configured to capture a current layer image of a current overlay mark on a current layer with the current focal length and capture a previous layer image of a previous overlay mark on the previous layer with the previous focal length; and a calculating unit configured to determine an overlay error between the current overlay mark and the previous overlay mark based on the current layer image and the previous layer image; and a controller configured to determine at least one parameter of an operating recipe for performing a photolithography process based on the overlay error.

15. The overlay control system of claim 14, wherein the metrology tool further comprises:

an ellipsometer configured to measure the thickness of the previous layer, the coefficient related to the material of the previous layer, or both of them, and the previous focus unit determines the previous focal length based on at least the measured thickness of the previous layer, the measured coefficient related to the material of the previous layer, or both of them.

16. The overlay control system of claim 14, wherein the metrology tool further comprises:

an ellipsometer configured to measure the thickness of the dielectric layer, the coefficient related to the material of the dielectric layer, or both of them, and the previous focus unit determines the previous focal length based on at least the measured thickness of the dielectric layer, the measured coefficient related to the material of the dielectric layer, or both of them.

17. The overlay control system of claim 14, wherein the metrology tool further comprises:

an ellipsometer configured to measure a dielectric constant of the previous layer, a refractive index of the previous layer or both of them, and the previous focus unit determines the previous focal length based on at least the measured dielectric constant of the previous layer, the measured refractive index of the previous layer or both of them.

18. The overlay control system of claim 14, wherein the metrology tool further comprises:

an ellipsometer configured to measure a dielectric constant of the dielectric layer, a refractive index of the dielectric layer or both of them, and the previous focus unit determines the previous focal length based on at least the measured dielectric constant of the dielectric layer, the measured refractive index of the dielectric layer or both of them.

19. An overlay control system, comprising:

a metrology tool comprising:

a current focus unit configured to determine a current focal length;

a previous focus unit configured to determine a previous focal length by an equation:

$$F_P = F_c + \alpha T,$$

wherein $F_P$ is the previous focal length, $F_c$ is the current focal length, $\alpha$ is a coefficient related to a material of a previous layer, a dielectric layer adjacent to the previous layer, or both of them, T is a thickness of the previous layer, the dielectric layer, or both of them;

at least one image capturing unit configured to capture a current layer image of a current overlay mark on a current layer with the current focal length and capture a previous layer image of a previous overlay mark on the previous layer with the previous focal length;

a calculating unit configured to determine an overlay error between the current overlay mark and the previous overlay mark based on the current layer image and the previous layer image; and a controller configured to determine at least one parameter of an operating recipe for performing a photolithography process based on the overlay error.

20. The overlay control system of claim 19, wherein the current focus unit is an autofocus system.

* * * * *